United States Patent [19]

Jahns et al.

[11] Patent Number: 5,596,051
[45] Date of Patent: Jan. 21, 1997

[54] MICROCAPSULES, THE PRODUCTION AND USE THEREOF

[75] Inventors: Ekkehard Jahns, Hirschberg; Burkhardt Dames, Neuwied, both of Germany

[73] Assignee: BASF Aktiengesellschaft, Ludwigshafen, Germany

[21] Appl. No.: 265,211

[22] Filed: Jun. 24, 1994

[30] Foreign Application Priority Data

Jun. 25, 1993 [DE] Germany .......................... 43 21 205.0

[51] Int. Cl.$^6$ .............................. C08F 2/00; B32B 5/16; B32B 9/02; B32B 9/04
[52] U.S. Cl. .................. 526/73; 526/319; 526/323.1; 526/323.2; 428/402.2; 428/402.21; 428/402.22
[58] Field of Search ..................... 526/73, 319, 323.1, 526/323.2; 428/402.2, 402.21, 402.22

[56] References Cited

U.S. PATENT DOCUMENTS

| 4,798,691 | 1/1989 | Kasai et al. |
| 4,908,271 | 3/1990 | Kasai et al. |
| 5,292,835 | 3/1994 | Jahns et al. ............... 526/73 |

*Primary Examiner*—Nathan M. Nutter
*Attorney, Agent, or Firm*—Oblon, Spivak, McClelland, Maier & Neustadt, P.C.

[57] ABSTRACT

Microcapsules which are composed of a core and of a shell of a polymer, the core containing at least one oil which can be emulsified in water, and which are obtainable by polymerization of oil-soluble monomer mixtures which contain (a) 1–100% by weight of acrylic anhydride, methacryic anhydride, itaconic anhydride, citraconic anhydride, dimethylmaleic anhydride, 4-vinylbenzoic anhydride, mixed carboxylic anhydrides, mixtures of the said anhydrides and/or more than 40% by weight of maleic anhydride, (b) 0–99% by weight of at least one monoethylenically unsaturated monomer which is different from the monomers of group (a), (c) 0–80% by weight of crosslinking monomers which have at least two monoethylenically unsaturated non-conjugated double bonds in the molecule, and (d) 0–20% by weight of water-soluble monoethylenically unsaturated monomers in the oil phase of a stable oil-in-water emulsion in the presence of polymerization initiators which form free radicals, where the temperature of the polymerizing reaction mixture may be continuously or periodically increased during the polymerization, a process for producing the microcapsules by polymerization of the abovementioned monomer mixtures in the oil phase of a stable oil-in-water emulsion in the presence of polymerization initiators which form free radicals, where the temperature of the polymerizing reaction mixture may be continuously or periodically increased during the polymerization, and the use of the microcapsules for the controlled release of the core material of the microcapsules as active substance by destruction of their shell, in particular by the action of bases.

12 Claims, No Drawings

MICROCAPSULES, THE PRODUCTION AND USE THEREOF

The present invention relates to microcapsules which are composed of a core and of a shell of a polymer, the core containing at least one oil which can be emulsified in water, to a process for the production of the microcapsules by polymerization of oil-soluble monomers in the oil phase of a stable oil-in-water emulsion in the presence of polymerization initiators which form free radicals, and to the use of the microcapsules for the controlled release of the core material of the microcapsules as active substance by destruction of their shell.

EP-B 0 198 089 discloses microcapsules which contain as core material an oil such as toluene and as shell a crosslinked polymer. According to the statements in Example 1, particles of this type are produced by polymerizing a solution of 4-vinylpyridine, divinylbenzene, styrene and n-butyl acrylate in toluene in the form of an oil-in-water emulsion in the presence of 3,5,5trimethylhexanoyl peroxide as polymerization initiator. The microcapsules have an average diameter of 10 μm. The oil phase can be removed from the particles by storage in air or by heating. The result is hollow particles which can be used as filler or as light-scattering polymeric white pigment.

EP-A 0 457 154 discloses microcapsules which are produced by emulsifying a mixture of a hydrocarbon oil, alkyl acrylates and, where appropriate, crosslinkers in water and polymerizing the resulting oil-in-water emulsion in the presence of polymerization initiators. The oil phase can contain, for example, color formers or other active substances. Microcapsules containing color formers are used, for example, for producing pressure-sensitive recording materials such as sets of forms. In the prior art the microcapsules are destroyed by pressure or heat and thus release the active substance present in the core.

It is an object of the present invention to provide microcapsules whose shell can additionally be opened by the action of reagents.

We have found that this object is achieved by microcapsules which are composed of a core and of a shell of a polymer, the core containing at least one oil which can be emulsified in water.

These microcapsules can be obtained by polymerizing oil-soluble monomer mixtures which contain (a) 1–100% by weight of acrylic anhydride, methacrylic anhydride, itaconic anhydride, citraconic anhydride, dimethylmaleic anhydride, 4-vinylbenzoic anhydride, mixed carboxylic anhydrides, mixtures of the said anhydrides and/or more than 40% by weight of maleic anhydride,
(b) 0–99% by weight of at least one monoethylenically unsaturated monomer which is different from the monomers of group (a),
(c) 0–80% by weight of crosslinking monomers which have at least two monoethylenically unsaturated non-conjugated double bonds in the molecule, and
(d) 0–20% by weight of water-soluble monoethylenically unsaturated monomers in the oil phase of a stable oil-in-water emulsion in the presence of polymerization initiators which form free radicals, where the temperature of the polymerizing reaction mixture may be continuously or periodically increased during the polymerization.

The present invention also relates to a process for producing microcapsules, which comprises polymerizing oil-soluble monomer mixtures which contain (a) 1–100% by weight of acrylic anhydride, methacrylic anhydride, itaconic anhydride, citraconic anhydride, dimethylmaleic anhydride, 4-vinylbenzoic anhydride, mixed carboxylic anhydrides, mixtures of the said anhydrides and/or more than 40% by weight of maleic anhydride,
(b) 0–99% by weight of at least one monoethylenically unsaturated monomer which is different from the monomers of Group (a),
(c) 0–80% by weight of crosslinking monomers which have at least two monoethylenically unsaturated non-conjugated double bonds in the molecule, and
(d) 0–20% by weight of water-soluble monoethylenically unsaturated monomers in the oil phase of a stable oil-in-water emulsion in the presence of initiators which form free radicals, where the temperature of the polymerizing reaction mixture may be continuously or periodically increased during the polymerization.

The present invention also relates to the use of the microcapsules described above for the controlled release of active substances which are present in the core material of the microcapsules by destruction of their shell as a consequence of the action of bases.

The shell of the microcapsules is composed of a polymer which contains carboxylic anhydride groups. Although the monomeric carboxylic anhydrides are very sensitive to hydrolysis and are converted simply on contact with water into the corresponding carboxylic acids, surprisingly the microcapsules obtained according to the invention contain anhydride groups in their polymer shell.

Suitable monomers of group (a) are 1–100% by weight of acrylic anhydride, methacrylic anhydride, itaconic anhydride, citraconic anhydride, dimethylmaleic anhydride, 4-vinylbenzoic anhydride or mixtures of the said anhydrides. It is, of course, also possible to employ mixed anhydrides, eg. those of acrylic and methacrylic acids, or of 4-vinylbenzoic and acrylic acids or of 4-vinylbenzoic and methacrylic acids. Also suitable as monomer of group (a) is maleic anhydride in amounts of at least 40% by weight. It can also be employed mixed with the other carboxylic anhydrides. Preferred monomers of component (a) are 45–100% by weight of acrylic anhydride and/or methacrylic anhydride.

When the monomers of group (b) are employed they can comprise up to 99% by weight of the monomer mixtures employed for the polymerization. These monomers are monoethylenically unsaturated and differ from the monomers of group (a) and do not react with the anhydride groups in the monomers (a) under the polymerization conditions. Examples of suitable monomers of this type are acrylic or methacrylic esters of monohydric $C_1$–$C_{24}$ –alcohols, for example methyl acrylate, methyl methacrylate, ethyl acrylate, ethyl methacrylate, n-propyl acrylate, n-propyl methacrylate, isopropyl acrylate, isopropyl methacrylate, n-butyl acrylate, isobutyl acrylate, tertbutyl acrylate, n-butyl methacrylate, isobutyl methacrylate, tert-butyl methacrylate, octyl acrylate, octyl methacrylate, 2-ethylhexyl acrylate, 2-ethylhexyl methacrylate, lauryl acrylate, lauryl methacrylate, stearyl acrylate, palmityl acrylate, stearyl methacrylate and palmityl methacrylate, styrene, α-methylstyrene, vinyl acetate, vinyl propionate, vinylpyridine, methacrylonitrile, methacrylamide, N-methylmethacrylamide, dimethylaminopropylmethacrylamide, cyclohexyl acrylate, cyclohexyl methacrylate, phenyl acrylate, phenyl methacrylate, dimethylaminoethyl acrylate, dimethylaminoethyl methacrylate, vinylcyclohexane, vinyl chloride, vinylidene chloride, 2-hydroxypropyl acrylate and 2-hydroxypropyl methacrylate.

When the monomers of group (b) are employed in the polymerization they are used in amounts of up to 99% by weight, preferably up to 60% by weight. Monomers of group (b) which are preferably employed are methyl methacrylate, methyl acrylate, ethyl acrylate, ethyl methacrylate, styrene, vinyl acetate and vinylpyridine.

Suitable monomers of group (c) are crosslinking monomers which contain at least two monoethylenically unsaturated non-conjugated double bonds in the molecule. Examples of compounds of this type are acrylic and methacrylic esters which are derived from dihydric alcohols containing 2–24 carbon atoms, eg. ethylene glycol diacrylate, ethylene glycol dimethacrylate, propylene glycol dimethacrylate, 1,4-butanediol diacrylate, 1,4-butanediol dimethacrylate, 1,6-hexanediol diacrylate and 1,6-hexanediol dimethacrylate, divinylbenzene, methallylmethacrylamide, allyl methacrylate, allyl acrylate, methylenebisacrylamide, trimethylolpropane triacrylate, trimethylolpropane trimethacrylate, pentaerythritol triallyl ether, pentaerythritol tetraacrylate and pentaerythritol tetramethacrylate. The monomers of group (c) can, like the monomers of groups (a) and (b), also be employed in the form of mixtures. When the monomers of group (c) are used they can comprise up to 80% by weight of the monomer mixture employed for the polymerization.

The monomers of group (c) preferably comprise up to 40% by weight of the monomer mixture employed for the polymerization. The effect of using these monomers is that the action of aqueous bases on the microcapsule walls does not completely dissolve them but only swells them to a greater or lesser extent. The swelling makes the microcapsule wall more permeable to the core material so that controlled release of the core material is possible over a longer period depending on the amount of crosslinker employed. In smaller amounts, i.e. up to about 10% by weight of monomer of group (c) in the monomer mixture, the effect of a crosslinker is to delay release of the core material and of the active substance dissolved therein where appropriate after hydrolysis of the shell of the microcapsules. Larger amounts of cross-linker generally lead to slower release of the core material on alkaline hydrolysis.

The shell of the microcapsules can be modified by including monomers of group (d) in the polymerization. Monomers of group (d) are polar and readily soluble in water. Examples of them are acrylic acid, methacrylic acid, acrylamide, hydroxyethyl acrylate, hydroxyethyl methacrylate, vinylsulfonic acid, acrylamidopropane-sulfonic acid, styrenesulfonic acid, sulfoethyl acrylate, sulfoethyl methacrylate, sulfopropyl acrylate, sulfopropyl methacrylate and acrylonitrile. This group of monomers can be present in the monomer mixtures employed for the polymerization and is used in amounts of up to 20% of the total weight of monomers employed.

The core of the microcapsules contains at least one oil which can be emulsified in water. This oil is the solvent for the monomer mixtures (a) with or without (b) and/or (c) and/or (d) employed in the polymerization. It forms the oil phase of the oil-in-water emulsion present in the polymerization. It is possible to employ as oil phase in principle all substances which can be emulsified as liquids in water at temperatures between their melting point and the boiling point of water. Suitable substances are all types of oils such as vegetable oils, animal oils, mineral oils, paraffins, chlorinated paraffins, fluorocarbons and other synthetic oils. Typical examples are sunflower oil, rapeseed oil, olive oil, peanut oil, soybean oil, kerosine, benzene, toluene, butane, pentane, hexane, cyclohexane, chloroform, tetrachloromethane, chlorinated diphenyls and silicone oils. High-boiling oils can also be used as core material, eg. dibutyl phthalate, diisohexyl phthalate, dioctyl phthalate, alkylnaphthalenes, dodecylbenzene, terphenyl and partially hydrogenated terphenyls. Apart from the said predominantly low molecular weight oily substances it is also possible to use polymers as core of the microcapsules or as oil phase of the oil-in-water emulsion in the polymerization as long as the polymers can be emulsified in water. This condition is generally met when the glass transition temperature of the polymers is below the temperature at which the polymers are emulsified in water. Examples of such polymers are acrylic esters derived from monohydric $C_1$–$C_{20}$-alcohols, methacrylic esters derived from monohydric $C_3$–$C_{20}$-alcohols, copolymers of styrene and styrene derivatives in which the comonomers used are the said alkyl acrylates or methacrylates, and hydrophobic polyesters, polyamides and polycarbonates. Suitable examples are poly(butyl acrylate), poly-(ethylhexyl acrylate), poly(styrene-co-n-butyl acrylate) and cold-polymerized poly (styrene-co-butadiene). It is also possible to use as oil phase mixtures of a plurality of oils or mixtures of oils and the polymers which can be emulsified in water. The oil phase may additionally contain active substances which are soluble therein, eg. drugs, enzymes, coloring agents, toner components, inks, rust preventatives, recording materials, catalysts, magnetic substances or crop protection agents. The oil phase which contains the monomers and, where appropriate, active substances comprises 20–65, preferably 30–60, % by weight of the oil-in-water emulsion subjected to the polymerization. A stable oil-in-water emulsion is required for the production of the microcapsules according to the invention. Emulsifiers are used to stabilize the emulsions. Preferred emulsifiers for this purpose are water-soluble polymers which usually reduce the surface tension of the water from 73 mN/m to 40–70 mN/m and thus ensure that the capsule walls are closed. High-shear stirrers can be used to produce with these polymers microcapsules with diameters of about 0.5–100 μm. Microcapsules with a diameter of up to 1000 μm can also be produced using stirrers with less shear.

Protective colloids are likewise used to stabilize the oil-in-water emulsion or the oil-in-water suspension resulting from the polymerization. Preferred protective colloids are cellulose derivatives such as hydroxyethylcellulose, carboxymethylcellulose and methylcellulose, and polyvinylpyrrolidone and copolymers of N-vinylpyrrolidone, polyvinyl alcohol and partially hydrolyzed polyvinyl acetates. It is also possible to employ gelatin, gum arabic, xanthan, sodium alginate, pectins and casein. The protective colloids are employed either alone or else in the form of mixtures of various protective colloids in amounts of 0.1–10, preferably of 0.5–5, % of the weight of the aqueous phase of the emulsion.

The stability of the emulsions can also be improved by using ionic emulsifiers. It may be particularly important to use ionic emulsifiers when there is a high content of microcapsules in the dispersion because there may easily be agglomeration of microcapsules without an additional ionic stabilizer. Suitable and preferred ionic emulsifiers are polyacrylic acid, polymethacrylic acid, copolymers of acrylic acid and methacrylic acid, sulfo-containing, water-soluble polymers such as polymers of sulfoethyl acrylate, sulfoethyl methacrylate or sulfopropyl methacrylate, and polymers of N-(sulfoethyl)maleimide, 2-acrylamido-2-alkylsulfonic acids, styrenesulfonic acid and vinylsulfonic acid. Also suitable are naphthalenesulfonic acid and condensates of naphthalenesulfonic acid and formaldehyde, as well as condensates of phenolsulfonic acid and formaldehyde. The ionic emulsifiers are usually added in amounts of 0.1–10% of the weight of the aqueous phase of the emulsion. The polymers of monoethylenically unsaturated carboxylic acids or monoethylenically unsaturated sulfonic acids which are used as emulsifiers have average molecular weights of from 500 to 1,000,000, preferably 1000 to 500,000.

The molecular weight of the polymers of which the shell is composed can be regulated by using the molecular weight regulators or chain-transfer agents which are normally suitable. These are oil-soluble compounds. Examples of suitable compounds of this type are mercaptans such as mercaptoethanol, mercaptopropanol, mercapto-butanols, n-dodecyl mercaptan, mercaptosuccinic acid, mercaptopropionic acid, mercaptoglycerol, mercaptoacetic acid, esters of thioglycolic acid such as hexyl thioglycolate, mercaptoalkylsilanes such as 3-mercapto-propyltrimethoxysilane and 3-mercaptopropyl(methyl)dimethoxysilane, ethers such as dioxane, tetrahydrofuran, tetrahydrofurfuryl alcohol, tetrahydrofurfuryl acetate, alcohols such as isopropanol, n-butanol and n-decanol and aromatic hydrocarbons such as isopropylbenzene.

Preferred regulators are esters of thioglycolic acid such as ethylhexyl thioglycolate and hexyl thioglycolate as well as dodecyl mercaptan. If regulators are used in the polymerization their amount is preferably 0.05–1.5% of the total weight of monomers.

The polymerization takes place in the presence of initiators which form free radicals. It is possible to use for this purpose all conventional peroxo and azo compounds in the amounts conventionally employed, eg. 0.1–5% of the weight of the monomers. Preferred polymerization initiators are those which are soluble in the oil phase or in the monomers. Examples of these are t-butyl peroxyneodecanoate, t-amyl peroxypivalate, dilauroyl peroxide, t-amyl peroxy-2-ethylhexanoate, 2,2'-azobis(2,4-dimethylvaleronitrile), 2,2'-azobis(2-methylbutyro-nitrile), dibenzoyl peroxide, t-butyl per-2-ethylhexanoate, di-t-butyl hydroperoxide, 2,5-dimethyl-2,5-di (t-butylperoxy)hexane and cumene hydroperoxide. Preferred radical initiators are di(3,5,5-trimethylhexanoyl) peroxide, 4,4'-azobisisobutyronitrile, t-butyl perpivalate and dimethyl 2,2'-azobisisobutyrate. These initiators have a half life of 10 hours in the range from 30 to 100° C. It is also possible to use water-soluble polymerization initiators or combinations of oil-soluble and water-soluble polymerization initiators.

The polymerization takes place in the oil phase of a stable oil-in-water emulsion. This emulsion is obtained by, for example, first dissolving the monomers and the polymerization initiator and, where appropriate, a polymerization regulator and an emulsifier in an oil, and emulsifying the resulting solution in water. The oil phase may additionally contain an active substance, eg. an enzyme. However, it is also possible initially to emulsify at least one oil in water and then add to the emulsion the monomers and the radical initiator and, where appropriate, the other auxiliaries such as protective colloids or polymerization regulators. In another variant it is also possible to emulsify the oil and the monomers in water and subsequently add only the polymerization initiator. The oil phase may in all cases contain other ingredients where appropriate, eg. drugs or color formers. Since the intention is to microencapsulate the oil phase in the emulsion as completely as possible, it is preferable to employ only those oils whose solubility in water is not too high. The solubility ought preferably not to exceed 5% by weight. For complete microencapsulation of the oil phase of the oil-in-water emulsion it is expedient to select the monomers on the basis of their solubility in the oil which is employed. Whereas the monomers are essentially soluble in the oil, polymerization thereof in the individual oil droplets results in polymers which are soluble neither in the oil phase nor in the aqueous phase of the oil-in-water emulsion and thus migrate to the interface between the oil droplets and the aqueous phase and thus form the wall material which finally envelops the oily core of the microcapsules.

The polymerization of the oil-in-water emulsion is normally carried out at 20–100, preferably 40°–90° C. The polymerization is normally carried out under atmospheric pressure but can also take place under reduced or elevated pressure, eg. in the range from 0.5 to 20 bar. The procedure is usually such that a mixture of water, protective colloids and/or emulsifiers, oily core materials with or without ingredients dissolved therein, radical initiators and monomers is emulsified with a high-speed disperser to give the required size, and the stable emulsion is heated with stirring to the decomposition temperature of the radical initiators. The rate of the polymerization can moreover be controlled by the choice of the temperature and the amount of the radical initiator in a conventional way. After the polymerization temperature is reached the polymerization is expediently continued for from 2 to 6 hours in order to complete the reaction of the monomers. Monomer mixtures which contain (a) 45–100% by weight of acrylic anhydride and/or methacrylic anhydride and
(b) 0–60% by weight of methyl methacrylate are preferably polymerized.

A particularly preferred procedure is to increase the temperature of the polymerizing reaction mixture continuously or periodically during the polymerization. This takes place by using a program with increasing temperature. The complete polymerization time can be divided for this purpose into at least two periods. In the first polymerization period there is slow decomposition of the radical initiators. In the second and, where appropriate, subsequent polymerization periods the temperature of the reaction mixture is increased so that there is faster decomposition of the radical initiators. The temperature can be increased in one step or in a plurality of steps or continuously in a linear or non-linear manner. The temperature difference between the start and end of the polymerization can be up to 50° C. In general, this difference is 3–40, preferably 3°–30° C. It is not at present possible to explain why the use of a program with increasing temperature during the polymerization results in microcapsules which are better than those from a polymerization at approximately constant temperature. However, it is assumed that the reason is to be found in the very complex process of polymerization with simultaneous phase separation inside the microcapsules.

The optimal temperature program may vary depending on the particular system of monomers and oil phase and cannot be predicted but must be found by experimentation. When a program with increasing temperature is used during the polymerization, the decomposition of a radical initiator in the first period with a low polymerization temperature will be only slow. However, a small number of radicals per unit time means that only a few polymer chains will start and will therefore be able to reach a high molecular weight. Chains of high molecular weight ought very quickly to show a phase separation from the oily core. This rapid phase separation may be unfavorable for uniform deposition of the wall material of the microcapsules. It therefore appears worthwhile in many cases to regulate the molecular weight by using molecular weight regulators or chain-transfer agents.

The microcapsules according to the invention are suitable for all known applications in which microcapsules are opened by pressure or elevated temperature and release the protected contents. It is possible, for example, to microencapsulate dyes, pigments, detergent auxiliaries, antifoam agents, inks, perfumes, foodstuffs, enzymes, liquid crystals, coloring agents, toner components, rust preventatives, recording materials, catalysts, magnetic substances, chemical reactants and solids which are insoluble in water, and for all applications of controlled release of the core material of the microcapsules as active substance by destruction of their shell.

In addition to the known methods for opening or destroying the shell of the microcapsules, in the case of the microcapsules according to the invention the destruction of the shell can be brought about by the action of bases. Examples of such applications are microencapsulated adhesives, detergent auxiliaries and antifoam agents. The microencapsulated adhesives can be activated, for example, by adjusting an aqueous microcapsule dispersion to a pH>7, preferably >9, with an aqueous base such as sodium hydroxide solution, and subsequently spreading the alkaline microcapsule dispersion on a substrate, eg. paper or a sheet. It is also possible to spread a microcapsule dispersion on a substrate and only then to treat it with a base in order to release the adhesive. Suitable bases are sodium and potassium hydroxide solutions, sodium and potassium carbonates, ammonia, amines, calcium hydroxide and barium hydroxide. The microcapsules according to the invention which contain in their core, for example, adhesives or detergent auxiliaries which are to be protected can also be added to a system which already has an alkaline pH, for example cement slurries or wash liquors.

The microcapsules according to the invention result from the production process according to the invention in the form of dispersions with a solids content of about 65–20, preferably 60–30, % by weight. These dispersions can be used immediately, or the microcapsules are isolated from the dispersions, for example by subjecting the dispersions to spray drying.

The K values stated in the examples are determined by the method of H. Fikentscher, Cellulose-Chemie, 13, (1932) 58–64 and 71–74 in a 1% strength aqueous solution at 25° C.

EXAMPLES

Example 1

Alkali-soluble microcapsules with an adhesive resin as core
A mixture of 499 g of water
12.5 g of polyvinylpyrrolidone of K value 90
12.5 g of polyvinyl alcohol (88% hydrolyzed, average molecular weight 128,000)
300 g of a poly(n-butyl acrylate) resin (Mw = 15,000, DIN 53019 viscosity = 25 Pas at 20°)
4 g of methyl methacrylate
3.5 g of methacrylic anhydride
0.1 g of t-butyl perpivalate is dispersed with a high-speed dissolver plate at room temperature for 20 minutes. The result is a stable oil-in-water emulsion of particles with a diameter of 1–60 µm. This emulsion is heated while stirring with an anchor stirrer to 59° C. The temperature of the oil-in-water emulsion is then increased to 63° over the course of one hour and to 80° C. over the course of a further 3 hours. It is subsequently cooled. The resulting microcapsule dispersion has a solids content of 36.2%.

A polyester sheet was coated with this dispersion and the coating was dried at room temperature. The coated sheet has virtually no tackiness.

A strip of the dried sheet was immersed in an aqueous NaOH solution of pH 12 for some hours and then dried. The coated sheet treated in this way is extremely tacky, which shows that the microcapsule wall has dissolved. The tackiness of the alkali-treated sheet is the same as that of a sheet from a comparison test in which the butyl acrylate resin was dispersed without auxiliaries in a polyvinyl alcohol solution and then coated onto the sheet.

Example 2

Alkali-soluble microcapsules with a silicone oil as core
A mixture of 237.5 g of water
6.25 g of polyvinylpyrrolidone of K value 90
6.25 g of polyvinyl alcohol (88% hydrolyzed, average molecular weight 128,000)
150 g of a polydimethylsiloxane with a viscosity of 230 mPas (measured at 20° C.)
2 g of methyl methacrylate
1.75 g of methacrylic anhydride
0.05 g of t-butyl perpivalate is dispersed with a high-speed dissolver plate at room temperature for 20 minutes. The result is a stable oil-in-water emulsion of particles with a diameter of 2–8 µm. This emulsion is heated while stirring with an anchor stirrer to 59° C. The temperature of the oil-in-water emulsion is then increased to 63° over the course of one hour and to 80° C. over the course of a further 3 hours. It is subsequently cooled. The resulting microcapsule dispersion has a solids content of 38.2%.

Example 3

Alkali-soluble microcapsules with an adhesive resin as core
A mixture of 499 g of water
12.5 g of polyvinylpyrrolidone of K value 90
12.5 g of polyvinyl alcohol (88% hydrolyzed, average molecular weight 128,000)
300 g of a poly(n-butyl acrylate) resin (Mw = 15,000, DIN 53019 viscosity = 25 Pas at 20°)
7.5 g of methacrylic anhydride
0.1 g of t-butyl perpivalate is dispersed with a high-speed dissolver plate at room temperature for 20 minutes. The result is a stable oil-in-water emulsion of particles with a diameter of 1–80 µm. This emulsion is heated while stirring with an anchor stirring to 59° C. The temperature of the oil-in-water emulsion is then increased to 63° over the course of one hour and to 80° C. over the course of a further 3 hours. It is subsequently cooled. The resulting microcapsule dispersion has a solids content of 38.5%.

When this dispersion is used to coat a polyester sheet and the coated sheet is dried at room temperature the coating is not tacky.

A strip of the dried coated sheet was immersed in an aqueous NaOH solution of pH 12 for five minutes and then dried. The coated sheet treated in this way is extremely tacky, which shows that the microcapsule wall has dissolved.

We claim:
1. A microcapsule comprising a core and a shell of a polymer, the core containing at least one oil which can be emulsified in water, said capsule prepared by polymerizing:
   (a) 1–100% by weight, based on the total weight of monomers (a) to (d), of acrylic anhydride, methacrylate anhydride, itaconic anhydride, citraconic anhydride, dimethylmaleic anhydride, 4-vinylbenzoic anhydride mixed carboxylic anhydrides, or mixtures thereof.
   (b) 0–99% by weight, based on the total weight of monomers (a) to (d), of at least one monoethylenically unsaturated monomer which is oil-soluble and which is different from the monomers of group (a),
   (c) 0–80% by weight, based on the total weight of monomers (a) to (d), of crosslinking monomers which are oil soluble and different from (a) which have at least two monoethylenically unsaturated non-conjugated double bonds in the molecule, and
   (d) 0–20% by weight, based on the total weight of monomers (a) to (d), of water-soluble monoethylenically unsaturated monomers,
   in the oil phase of a stable oil-in-water emulsion in the presence of polymerization initiators which form free radicals, where the temperature of the polymerizing reaction mixture may be continuously or periodically increased during the polymerization.

2. A process for producing microcapsules which comprises polymerizing
   (a) 1–100% by weight, based on the total weight of monomers (a) to (d), of acrylic anhydride, methacrylate anhydride, itaconic anhydride, citraconic anhydride, dimethylmaleic anhydride, 4-vinylbenzoic anhydride, mixed carboxylic anhydrides, or mixtures thereof,
   (b) 0–99% by weight, based on the total weight of monomers (a) to (d), of at least one monoethylenically unsaturated monomer which is oil-soluble and which is different from the monomers of group (a),
   (c) 0–80% by weight, based on the total weight of monomers (a) to (d), of crosslinking monomers which are oil soluble and different from (a) which have at least two monoethylenically unsaturated non-conjugated double bonds in the molecule, and
   (d) 0–20% by weight, based on the total weight of monomers (a) to (d), of water-soluble monoethylenically unsaturated monomers,
   in the oil phase of a stable oil-in-water emulsion in the presence of polymerization initiators which form free radicals, where the temperature of the polymerizing reaction mixture may be continuously or periodically increased during the polymerization.

3. The process as claimed in claim 2, comprising polymerizing:
   (a) 45–100% by weight of acrylic anhydride and/or methacrylic anhydride and
   (b) 0–60% by weight of methyl methacrylate.

4. The microcapsule of claim 1, comprising 0–60% by weight of monomers (b).

5. The microcapsule of claim 1, wherein monomer (b) is selected from the group consisting of methyl methacrylate, methyl acrylate, ethyl acrylate, ethyl methacrylate, styrene, vinyl acetate and vinyl pyridine.

6. The microcapsule of claim 1, comprising 0–40% by weight of monomers (c).

7. The microcapsule of claim 1, wherein monomer (c) is selected from the group consisting of ethylene glycol diacrylate, ethylene glycol dimethacrylate, propylene glycol dimethacrylate, 1,4-butanediol diacrylate, 1,4-butanediol dimethacrylate, divinylbenzene, methallylmethacrylamide, allyl methacrylate, allyl acrylate, methylenebisacrylamide, trimethylolpropane triacrylate, trimethylolpropane trimethacrylate, pentaerythritol triallyl ether, pentaerythritol tetraacrylate and pentaerythritol tetramethacrylate.

8. The microcapsule of claim 1, wherein monomer (d) is selected from the group consisting of acrylic acid, methacrylic acid, acrylamide, hydroxyethyl acrylate, hydroxyethyl methacrylate, vinylsulfonic acid, acrylamidopropanesulfonic acid, styrenesulfonic acid, sulfoethyl acrylate, sulfoethyl methacrylate, sulfopropyl acrylate, sulfopropyl methacrylate and acrylonitrile.

9. A microcapsule comprising a core and a shell of a polymer, the core containing at least one oil which can be emulsified in water, said capsule prepared by polymerizing:
   (a) more than 40% by weight of maleic anhydride,
   (b) 0–99% by weight of at least one monoethylenically unsaturated monomer which is oil-soluble and which is different from the monomers of group (a),
   (c) 0–80% by weight of crosslinking monomers which are oil soluble and different from (a) which have at least two monoethylenically unsaturated non-conjugated double bonds in the molecule, and
   (d) 0–20% by weight of water-soluble monoethylenically unsaturated monomers the percentages relating to the total amount of monomers (a) to (d), in the oil phase of a stable oil-in-water emulsion in the presence of polymerization initiators which form free radicals, where the temperature of the polymerizing reaction mixture may be continuously or periodically increased during the polymerization.

10. The microcapsule of claim 9, wherein component (a) further comprises acrylic anhydride, methacrylate anhydride, itaconic anhydride, citraconic anhydride, dimethylmaleic anhydride, 4-vinylbenzoic anhydride, mixed carboxylic anhydrides, or mixtures thereof.

11. A process for producing microcapsules which comprises polymerizing
   (a) more than 40% by weight of maleic anhydride,
   (b) 0–99% by weight of at least one monoethylenically unsaturated monomer which is oil-soluble and which is different from the monomers of group (a),
   (c) 0–80% by weight of crosslinking monomers which are oil soluble and different from (a) which have at least two monoethylenically unsaturated non-conjugated double bonds in the molecule, and
   (d) 0–20% by weight of water-soluble monoethylenically unsaturated monomers the percentages relating to the total amount of monomers (a) to (d),
   in the oil phase of a stable oil-in-water emulsion in the presence of polymerization initiators which form free radicals, where the temperature of the polymerizing reaction mixture may be continuously or periodically increased during the polymerization.

12. The process of claim 11, wherein component (a) further comprises acrylic anhydride, methacrylate anhydride, itaconic anhydride, citraconic anhydride, dimethylmaleic anhydride, 4-vinylbenzoic anhydride, mixed carboxylic anhydrides, or mixtures thereof.

* * * * *